United States Patent [19]

List et al.

[11] 3,965,383

[45] June 22, 1976

[54] MULTI-WIRE OXYGEN ELECTRODE AND METHOD OF MANUFACTURING THE SAME

[75] Inventors: Helmut List; George Fredericks, both of Graz, Austria

[73] Assignee: AVL AG, Schaffhausen, Switzerland

[22] Filed: Mar. 6, 1975

[21] Appl. No.: 555,767

[30] Foreign Application Priority Data

Mar. 15, 1974 Switzerland.......................... 3642/74

[52] U.S. Cl............................... 313/331; 313/332; 313/333; 313/337
[51] Int. Cl.² ......................................... H01J 5/50
[58] Field of Search .......... 313/331, 332, 333, 274, 313/278, 337

[56] References Cited
UNITED STATES PATENTS

| | | | |
|---|---|---|---|
| 2,222,669 | 11/1940 | Kurtz | 313/331 X |
| 2,317,143 | 4/1943 | Goodale | 313/331 |
| 3,040,204 | 6/1962 | Belknap | 313/274 X |

Primary Examiner—Saxfield Chatmon, Jr.
Attorney, Agent, or Firm—Ladas, Parry, Von Gehr, Goldsmith & Deschamps

[57] ABSTRACT

A multi-wire oxygen electrode and method of manufacturing the same, said electrode having a reactive electrode surface formed by a glass electrode tip having an end surface and a number of electrode wires are distributed in the end surface of the electrode tip along a circle. The cross-sectional surface of said electrode wires are freely exposed in such end surface and the electrode wires are fused in the electrode tip and electrically conductively connected with a cathode wire arranged in a glass sleeve. There is provided a substantially semi-spherical shaped support surface having an apex, said support surface being coaxially arranged with respect to the electrode tip, and said cathode wire being held in the electrode tip at the apex of the support surface. The electrode wires are electrically conductively secured at the cathode wire at the apex of the support surface, each electrode wire being guided through a substantially one-quarter arc over the support surface and then substantially parallel to the longitudinal axis of the electrode tip to its end surface.

7 Claims, 13 Drawing Figures

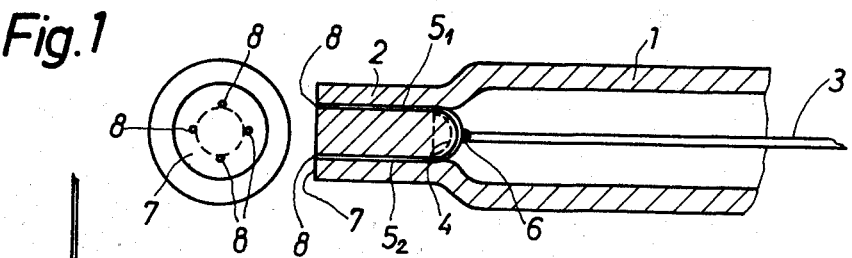

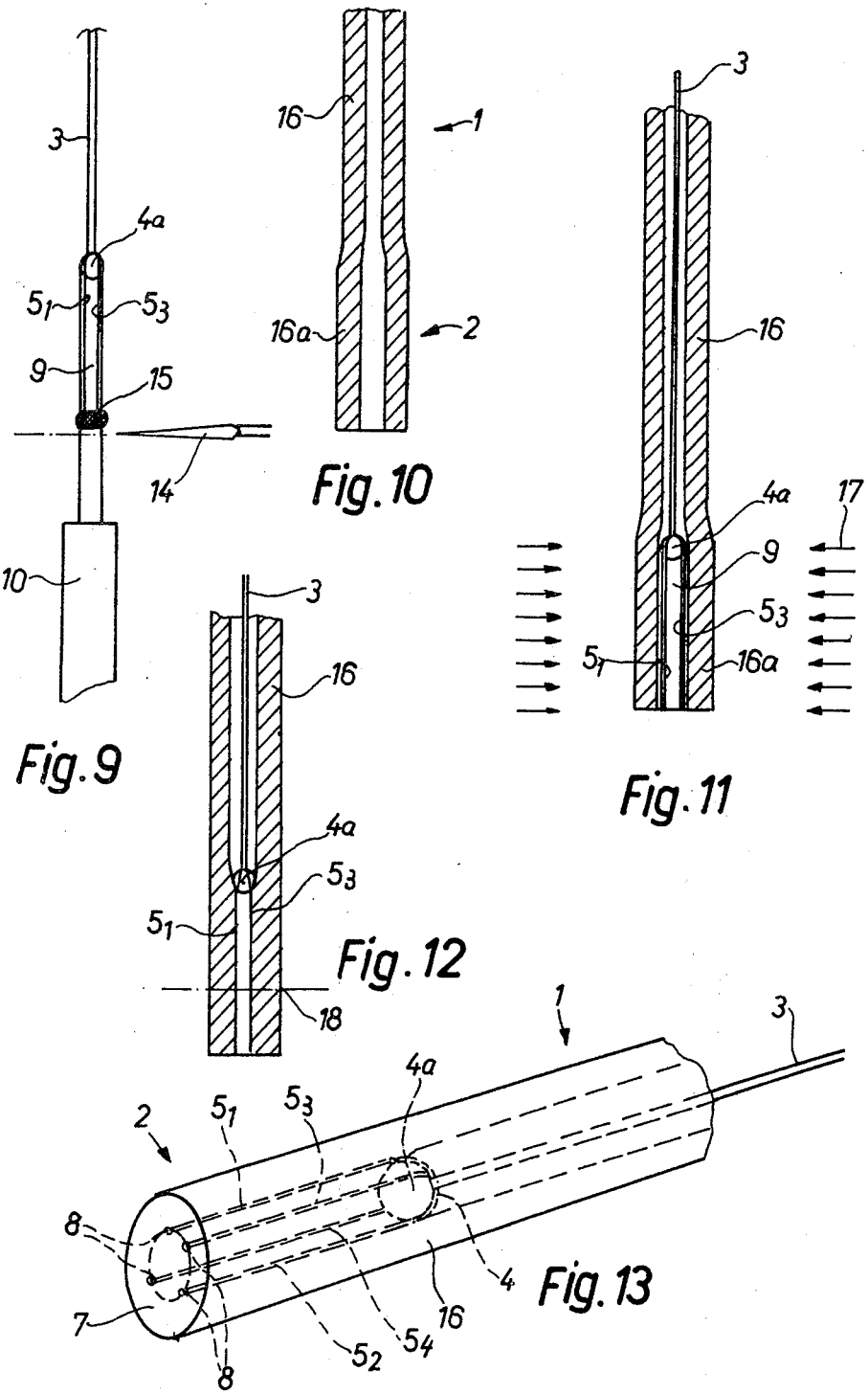

MULTI-WIRE OXYGEN ELECTRODE AND METHOD OF MANUFACTURING THE SAME

BACKGROUND OF THE INVENTION

The present invention relates to a new and improved construction of multi-wire oxygen electrode, the reactive electrode surface of which is formed from freely exposed cross-sectional surfaces of a number of electrode wires distributed along a circle and arranged in the end surface of an especially cylindrical electrode tip formed of glass and wherein the electrode wires fused in the electrode tip are electrically coupled with a cathode wire arranged in a glass sleeve or envelope. The invention further pertains to a novel method of manufacturing the aforesaid multi-wire oxygen electrode.

In the case of oxygen electrodes the cathode- and electrode wires are generally formed of platinum and the glass sleeves or envelopes with the electrode tips of glass, for instance lead glass or the trademark glass product known as "JENAER GLAS 16 III", which practically has the same thermal coefficient of expansion as platinum and a high specific electrical resistance for such electrochemical electrodes. At the end surface of the electrode tip there are uniformly distributed along a circular periphery the reactive regions formed by the freely exposed end surfaces of the electrode wires, so that they possess the same spacing from one another. The electrode wires for reasons of measurement technology are as thin as possible, their diameter amounts to for instance 0.01 millimeters, and are relatively long and they must be fused into the electrode tip smoothly, especially free of any kinks or bends and of course without any interruptions or ruptures, and additionally, they must be in good electrical contact with the cathode wire.

Owing to these requirements and the fineness of the structure of the electrode wires it is difficult to manufacture multi-wire oxygen electrodes. The fabrication is considerably facilitated by using platinum wire encased in glass, and which can be easily handled and is obtainable with good quality. Normally for this reason, for instance for the prior art four wire-oxygen electrodes four pieces of glass encased-platinum wires are fused together in a small glass tube into an electrode tip. The individual pieces of glass encased platinum wire can be easily checked for defects prior to the fusing together and with certain care during the fusing operation there are also obtained compact electrode tips which do not contain any capillary channels and in which there are arranged, as required, the electrode wires. In order to electrically connect the electrode wires with the cathode wire there is used in this case mercury. Above the electrode tip there is provided in the small glass tube a hollow compartment or space containing mercury and into which compartment there extend the ends of the electrode wires and the cathode wire. However the use of mercury for establishing the electrical contact is associated with drawbacks, both with respect to the fabrication of the oxygen electrodes since the safety measures which are required when handling mercury necessitate an additional expenditure, as well as also during the use of the finished oxygen electrodes since the usual shaking of the electrode prior to placing such into operation is bothersome but is required to insure for a faultless contact of all electrode wires with the cathode wire. Furthermore, electrodes which no longer can be used cannot simply be thrownaway, rather must be specially handled due to the presence of the mercury. Hence, it is for these reasons that multi-wire oxygen electrodes which do not contain any mercury would be of advantage in practice. However, such oxygen electrodes formed of glass encased electrode wires cannot be economically manufactured.

SUMMARY OF THE INVENTION

Hence, it is a primary object of the present invention to provide an improved construction of multi-wire oxygen electrode and a method of manufacturing the same which is not associated with the aforementioned drawbacks and limitations of the prior art proposals.

It is a further and more specific object of the invention to provide a multi-wire oxygen electrode wherein there are eliminated the drawbacks associated with the mercury contact by means of a fixed connection of the electrode wires with the cathode wire, and furthermore to provide a method for the fabrication of such multi-wire oxygen electrode which at least is not considerably more expensive and complicated than the techniques used for fabricating the state-of-the-art electrodes of this type.

Now in order to implement these and still further objects of the invention, which will become more readily apparent as the description proceeds, the multi-wire oxygen electrode of this development is manifested by the features that the cathode wire in the electrode tip is held at the apex or crown of a semi-spherical shaped support surface which is coaxial with respect to the electrode tip. The electrode wires are electrically conductively secured at the apex of the supporting surface at the cathode wire and each electrode wire is guided in a one-quarter arc over the support surface and then parallel to the axis of the electrode tip to its end surface. This attachment of the electrode wires at the cathode wire and guiding over the support surface insures for a positive and permanent electrical connection of the wires and renders possible also a simple fabrication of the oxygen electrode.

Not only is the invention concerned with the aforesaid novel construction of multi-wire oxygen electrode, but as mentioned above is also concerned with a novel method for manufacturing the same. This method contemplates that a cathode wire and a round glass rod are fixedly interconnected with one another at one end while forming a semi-spherical shaped transition of thinner cathode wire to thicker glass rod and electrode wires spanned at the semi-spherical shaped transition forming the support surface are electrically conductively secured at the cathode wire, the electrode wires are bent over the semi-spherical shaped transition-support surface, spanned along the glass rod and their ends bonded at the glass rod by means of an adhesive mass. Furthermore, the cathode wire with the glass rod and the electrode wires are inserted into a glass envelope or sleeve which possesses a tubular-shaped tip dimensioned for the reception of the glass rod with the electrode wires, and in the vertical position of the glass sleeve with the tip directed downwardly such is fused with the glass rod, and wherein the length of the glass rod and the wall thickness of the sleeve tip are selected such that during fusing the weight of the melt just compensates the surface forces causing a contraction of the melt and the electrode wires in glass are neither elongated nor curved, and that there is cut-off an end piece of the electrode tip fused with the glass rod in order to obtain the electrode end surface with the electrode wire-cross-sectional surfaces which are freely exposed in such electrode end surface.

The transition which provides the support or supporting surface can be fabricated in optional manner. The transition can simply be formed from a semi-spherical shaped rounded end of the glass rod and advantageously metalized in order to obtain a good electrical contact with the electrode wires. Of even greater advantage is to carry out the procedure wherein the cathode wire at one end is fused back into a sphere and then the cathode wire with the sphere or ball is fused at the glass rod. The electrode wires can be bonded at the cathode wire and also at the support surface by means of a metal colloid, such as conductive silver or conductive gold, which after heating provides a sturdy and electrically good conductive connection of cathode wire and electrode wires. The electrode tip can contain an even number of electrode wires, wherein each two respective wires are situated diametrically opposite one another. For each pair of diametrically oppositely situated electrode wires there can be employed a wire piece which bears in a streched state and with its center at the cathode wire tightly at the support surface and for instance bonded with conductive silver. As the adhesive mass for bonding the electrode wire ends at the glass rod there is advantageously employed a mixture of glass powder, gum arabic and water. The electrode wires secured at the cathode wire can be cut for the glass rod length determined for the compensation of the surface tension forces and the glass rod after the bonding of the electrode wire ends with the adhesive mass at the relevant location can be cut apart by means of a needle point flame or the like, wherein the adhesive mass is heated to such an extent that the glass powder melts and there do not remain any residues forming electrically conductive bridges.

BRIEF DESCRIPTION OF THE DRAWINGS

The invention will be better understood and objects other than those set forth above, will become apparent when consideration is given to the following detailed description thereof. Such description makes reference to the annexed drawings wherein:

FIG. 1 is a longitudinal fragmentary sectional view of a multi-wire oxygen electrode designed according to the teachings of the present invention;

FIGS. 2 to 12 illustrate respectively the different method steps employed for the fabrication of a four wire-oxygen electrode according to the invention; and FIG. 13 illustrates the four wire-oxygen electrode produced according to the method of this development.

DETAILED DESCRIPTION OF THE PREFERRED EMBODIMENTS

Describing now the drawings, the multi-wire oxygen electrode illustrated in enlarged longitudinal sectional view in FIG. 1 will be understood to comprise a glass sleeve or envelope 1 which terminates in a substantially cylindrical electrode tip 2. The cathode wire 3 held in the glass sleeve or envelope 1 is supported at the electrode tip 2 at the apex or crown of a substantially semi-spherical shaped support or supporting surface 4. The electrode wires $5_1$, $5_2$ are secured at the cathode wire 3 and specifically as tightly as possible at the supporting surface apex. The attachment location has been designated by reference character 6. Each electrode wire $5_1$, $5_2$ leads from the attachment location 6 in the form of a one-quarter arc over the semi-spherical shaped support surface 6 and then extends substantially parallel to the axis of the electrode tip 2 up to its end surface 7 where the wire cross-sections 8 are freely exposed.

The electrode wires $5_1$, $5_2$ are arranged in the electrode tip 2 in such a manner that their ends which are freely exposed in the end surface 7 are uniformly distributed about a circular circumference or periphery. As is conventional in the case of oxygen electrodes the cathode wire 3 and the electrode wires $5_1$, $5_2$ consist of platinum and as the material for the sleeve or envelope 1 and the electrode tip 2 there is employed a lead glass or lead crystal. The cathode wire 3 possesses, for instance, a diameter of 0.2 millimeters and for the electrode wires $5_1$, $5_2$ there is provided for instance a wire diameter of 0.01 millimeters. The length of the electrode tip 2 can be in the order of 1 centimeter, the diameter of the electrode end surface 7 amounts to 3 millimeters and the electrode wire-cross-sections or cross-sectional surfaces 8 which are freely exposed in the end surface 7 can be uniformly distributed about the circumference of a circle having a diameter of for instance about 1 millimeter. The semi-spherical shaped support surface 4 practically has the same diameter as the distribution circle and is formed from a material transition of smaller cathode wire cross-section to the larger distribution circle. The indicated dimensions have been randomly selected, but however correspond to a useful oxygen electrode. At this point it is to be therefore specifically mentioned that the dimensions given above are purely exemplary and in no way intended to be limiting of the invention. The material transition forming the support surface 4 can basically be produced in any given manner, what is however important is only that there are not caused thereby any stresses which would impair the service life of the electrode. The electrode tip can contain any useful number of electrode wires. Generally there are provided in such oxygen electrodes four electrode wires.

The fabrication of one such four wire-oxygen electrode of the type shown in FIG. 1 will be described hereinafter in detail in conjunction with the individual method steps.

There is used for the cathode wire 3 for instance an 80 millimeter long piece of pure platinum wire of a diameter of 0.2 millimeters. The platinum wire is annealed until it becomes flexible and one end of the wire is fused or melted with the aid of a flame into a small ball or sphere. At the one end of a circular rod of at least 30 millimeters length and having a diameter of 0.9 millimeters ± 0.05 millimeters there is fused a glass tube serving as a handle and at the other end the ball or sphere of the platinum wire. There is thus obtained the unit 11 shown in FIGS. 2 and 3 and composed of the cathode wire 3, the sphere or ball 4a, the glass rod 9 and the handle 10, and which unit can be easily handled and whereat the half of the sphere 4a bearing at the cathode wire 3 forms the semi-spherical shaped support surface 4.

The application of the electrode wires $5_1$, $5_2$ formed of thin platinum wire, having a diameter of 0.01 millimeters, advantageously occurs with the aid of a microscope. At the center of a spanned or stretched thin platinum wire 5 of about 30 millimeters length, and as shown in FIG. 3, there is applied the unit 11 in such a manner that the platinum wire 5, which extends perpendicular to the cathode wire 3, contactingly bears at the transition location of the cathode wire 3 into the sphere or ball 4a. In this position the platinum wire 5 is bonded at the cathode wire 3 and sphere 4a by means of a small droplet 12 of conductive silver; the two wire ends protruding from the sphere form the first pair of electrode wires $5_1$, $5_2$. Both of the wire pieces are shortened to about 10 millimeters and the wire 5 is then annealed at about 800°C with the aid of an electronically regulated current emanating from a network device 13, as best seen by referring to FIG. 4. The last steps are repeated with a second stretched or spanned platinum wire 5a, wherein the unit 11 is applied to the center of the second wire 5a in such a manner that the platinum wire 5a extends perpendicular to the cathode wire 3 and the first bonded platinum wire 5. The pieces of the second platinum wire 5a protruding from the cathode wire 3 form the second pair of electrode wires $5_3$, $5_4$. The unit 11 then has the configuration shown in FIG. 5 and it will be seen that from the point of application of the cathode wire 3 at the sphere 4a there protrude perpendicular to the cathode wire 3 four wires each of 1 centimeter length and which are aligned at right-angles to one another and bonded by means of conductive silver. During the development of the conductive silver it is preferable to proceed as follows: initially there is removed the glass rod 9 by means of a needle point flame at about 20 millimeters from the sphere or ball 4a, then the cathode wire 3 while in vertical position, with the glass rod 9 disposed downwardly, is heated with a needle point flame 14 about 15 millimeters above the sphere or ball 4a and as soon as the cathode wire 3 at this location glows red-hot the cathode wire is slowly drawn upwardly so that also the platinum sphere 4a begins to glow (FIG. 6). When the ball 4a glows then the flame 14 is removed, the fine platinum wires 5, 5a are then soldered at the cathode wire and sphere by the molten or fused silver. Thereafter there is again fused the glass tube 10 serving as the handle at the glass rod 9.

The next step during the fabrication of the four wire-oxygen electrode is portrayed in FIG. 7. While looking through a microscope the four electrode wires $5_1$, $5_2$, $5_3$, $5_4$ protruding from the sphere or ball 4a are in succession smoothly applied to the glass rod 9 such that they extend uniformly distributed about the circumference of the glass rod and in parallelism with respect to one another and their ends are bonded by means of an adhesive mass 15 at the glass rod 9. As the adhesive mass there is preferably employed a mixture of lead glass powder, water and gum arabic. FIG. 8 shows a section through the glass rod 9 at the region of the adhesive location. After the drying of the adhesive mass 15 the glass rod 9 is melted apart just below the adhesive location with the aid of a needle point flame 14. In this regard the adhesive mass 15 is heated to such an extent until the glass powder melts as seen in FIG. 9. After this operation the ends of the electrode wires $5_1$, $5_2$, $5_3$, $5_4$ bearing in the proper position and free of kinks or bends at the glass rod 9 are held at the end of the glass rod 9 in a glass embedding which is electrically insulating since the gum arabic leaves no residues whatsoever.

In FIG. 10 there is shown a longitudinal sectional view through the glass sleeve or envelope 1 with the tip 2 and used for this four wire-oxygen electrode. The glass sleeve or envelope 1 consists of, for instance, a lead glass tube having a length of about 105 millimeters and an outer diameter of 3 millimeters. The one end 16a of the glass tube 16 is formed with exact dimensions with a larger wall thickness and an internal diameter of 1 millimeter such that the glass rod 9 together with the bonded electrode wires $5_1$, $5_2$, $5_3$, $5_4$ (FIG. 9) has place therein.

As the next step during the manufacture of the four wire-oxygen electrode there then occurs the insertion of the unit (FIG. 9), consisting of the cathode wire 3, sphere 4a, glass rod 9 and the electrode wires $5_1$, $5_2$, $5_3$, $5_4$ bonded at the glass rod, into the glass tube 16 (FIG. 10) which is to be carried out while exercising a certain amount of care so as not to damage the fine electrode wires. Thereafter there occurs the fusing of the glass tube end 16a and glass rod 9 into the electrode tip. As best seen by referring to FIG. 11 for this purpose the glass tube 16 is held vertically with the glass rod 9 directed downwardly and with the aid of a flame, schematically indicated in FIG. 11 by the arrows 13, the glass tube end 16a is shrunk over the glass rod 9 until both components are completely fused together. After cutting at the adhesive location (FIG. 9) the glass rod 9 with a given diameter has such a length and the glass tube end 16a with the corresponding length such a wall thickness that during fusing of the glass rod 9 and glass tube end 16a the weight of the melt just compensates the effective surface tension forces and the melt neither contracts nor is the tip stretched. The mass of glass rod and glass tube end required for this purpose can be easily determined, for instance experimentally, and which need only be carried out once for the momentary or relevant type of oxygen electrode being produced. During the fusing the fine electrode wires are thus not mechanically loaded and with only very slight deviations they remain in the predetermined position.

After the fusing of the glass tube end 16a and glass rod 9 there is annealed as usual the tip for stress relief.

Finally, there is examined under the microscope the location in the tip where the electrode wires $5_1$, $5_2$, $5_3$, $5_4$ are distributed most uniformly about the circumference and there is cut-off at this location, indicated by reference character 18 in FIG. 12, the end of the electrode tip.

A four wire-oxygen electrode fabricated according to the above-described method has been shown in perspective view in FIG. 13. In the electrode end surface 7 obtained after cutting-off the tip end (FIG. 12) there are very uniformly distributed along a circumference of predetermined diameter the freely exposed cross-sectional surfaces or cross-sections 8 of the electrode wires $5_1$, $5_2$, $5_3$, $5_4$. In the compact electrode tip 2 consisting of a uniform glass melt there extend the electrode wires $5_1$, $5_2$, $5_3$, $5_4$ parallel to the tip lengthwise axis and the ends of the electrode wires which are guided over the semi-spherical shaped support surface 4 are directly electrically conductively connected at the cathode wire 3. The electrode-glass sleeve 1 has the same diameter as the electrode tip 2 which is several millimeters long. Therefore when necessary it is possible to cut-off a further tip end without there being required for this electrode with the shortened electrode tip changes at the electrode holder or support of the device. The guiding of the electrode wires $5_1$, $5_2$, $5_3$, $5_4$ over the semi-spherical shaped support surface 4 renders possible an easy handling of the fine electrode wires and prevents damaging the electrode wires during their alignment at the glass rod, since the electrode wires tangentially extend from the support surface and the attachment location is relieved. Due to the bonding with conductive silver there is additionally insured for a good electrically conductive and permanent connection of the electrode wires with the cathode wire.

The previously described fabrication technique of multi-wire oxygen electrode which has been discussed in detail on the basis of a single fabrication in a laboratory, while maintaining the essential steps, to wit, providing a semi-spherical shaped support surface, bonding the electrode wires with metal colloid at the cathode wire and the support surface at one end and attachment thereof with molten glass at the other end, as well as correct dimensioning of the electrode tip prior to the fusing, can be easily modified for mass production as well as also for an automatic fabrication.

While there is shown and described present preferred embodiments of the invention, it is to be distinctly understood that the invention is not limited thereto, but may be otherwise variously embodied and practiced within the scope of the following claims.

Accordingly, what is claimed is:

1. A multi-wire oxygen electrode, comprising a glass electrode tip having a reactive electrode surface at one end, a substantially semi-spherical support surface arranged coaxially with respect to the electrode tip at the other end thereof, a glass sleeve connected to the electrode tip at said other end, a cathode wire arranged in the glass sleeve and having one end held in the electrode tip at the apex of the support surface, and a number of electrode wires fused in said electrode tip, each electrode wire being secured at one end in electrically conductive manner to said one end of the cathode wire at the apex of the support surface, being guided through a substantially one-quarter arc over the support surface and then substantially parallel to the longitudinal axis of the electrode tip to said electrode surface, and having its other end freely exposed at said electrode surface, the exposed ends of the electrode wires being distributed about a circle.

2. The multi-wire oxygen electrode as defined in claim 1, wherein the electrode tip contains an even number of said electrode wires, each two respective electrode wires are substantially diametrically oppositely arranged in said electrode tip with respect to one another, and each pair of diametrically oppositely arranged electrode wires is constituted by a wire piece which is secured at its central region at the cathode wire.

3. The multi-wire oxygen electrode as defined in claim 1, wherein the cathode wire has an end carrying a metallic ball, the half of the ball confronting the cathode wire forming said support surface and the other half being fused in the electrode tip formed of glass.

4. The multi-wire oxygen electrode as defined in claim 3, wherein the metallic ball consists of a substantially spherical-shaped end of the cathode wire.

5. The multi-wire oxygen electrode as defined in claim 4, wherein the cathode wire and the electrode wires are formed of platinum and the electrode wires are secured at the cathode wire by conductive silver.

6. The multi-wire oxygen electrode as defined in claim 4, wherein the cathode wire and the electrode wires are formed of platinum and the electrode wires are secured at the cathode wire by conductive gold.

7. The multi-wire oxygen electrode as defined in claim 1, wherein the electrode tip with the electrode wires is constituted by an end piece of a substantially cylindrical glass tube and which end piece is filled with glas.

* * * * *